(12) United States Patent
Bunker et al.

(10) Patent No.: US 8,469,295 B2
(45) Date of Patent: Jun. 25, 2013

(54) TRACE CHEMICAL PARTICLE RELEASE NOZZLE

(75) Inventors: Stephen N. Bunker, Wakefield, MA (US); Keith A. Richards, Manchester, NH (US)

(73) Assignee: Implant Sciences Corporation, Wilmington, DE (US)

( * ) Notice: Subject to any disclaimer, the term of this patent is extended or adjusted under 35 U.S.C. 154(b) by 914 days.

(21) Appl. No.: 11/654,900

(22) Filed: Jan. 18, 2007

(65) Prior Publication Data

US 2007/0215725 A1 Sep. 20, 2007

Related U.S. Application Data

(63) Continuation-in-part of application No. 11/492,672, filed on Jul. 25, 2006, now abandoned, which is a continuation-in-part of application No. 11/258,477, filed on Oct. 25, 2005, now Pat. No. 8,122,756, and a continuation-in-part of application No. 10/890,820, filed on Jul. 14, 2004, now Pat. No. 7,098,672, which is a continuation-in-part of application No. 10/818,434, filed on Apr. 5, 2004, now Pat. No. 6,870,155, which is a continuation-in-part of application No. 10/349,491, filed on Jan. 22, 2003, now Pat. No. 6,828,795, which is a continuation-in-part of application No. 10/295,039, filed on Nov. 14, 2002, now abandoned, which is a continuation-in-part of application No. 10/295,010, filed on Nov. 14, 2002, now Pat. No. 6,861,646, application No. 11/654,900, which is a continuation-in-part of application No. 11/248,603, filed on Oct. 12, 2005, now Pat. No. 7,576,320, which is a continuation-in-part of application No. 10/853,563, filed on May 25, 2004, now Pat. No. 7,244,288, and a continuation-in-part of application No. 10/818,434, filed on Apr. 5, 2004, now Pat. No. 6,870,155, which is a continuation-in-part of application No. 10/754,088, filed on Jan. 7, 2004, now Pat. No. 6,888,128, which is a continuation-in-part of application No. 10/295,010, filed on Nov. 14, 2002, now Pat. No. 6,861,646, which is a continuation-in-part of application No. 10/890,820, filed on Jul. 14, 2002, now Pat. No. 7,098,672.

(60) Provisional application No. 60/363,485, filed on Mar. 12, 2002, provisional application No. 60/357,618, filed on Feb. 15, 2002, provisional application No. 60/357,394, filed on Feb. 15, 2002, provisional application No. 60/473,649, filed on May 28, 2003.

(51) Int. Cl.
*B05B 1/04* (2006.01)
*B05B 7/12* (2006.01)

(52) U.S. Cl.
USPC ........ 239/551; 239/416; 239/417.5; 239/418; 239/423

(58) Field of Classification Search
USPC .............. 239/551, 554, 416–417.5, 418, 423, 239/290, 291, 292, 299, 300, 413, 414, 415, 239/424, 424.5, 425; 134/18, 26, 30, 31, 134/34, 37, 42
See application file for complete search history.

(56) References Cited

U.S. PATENT DOCUMENTS 2,868,584 A * 1/1959 Faust ............................ 239/366
4,232,832 A * 11/1980 De Fusco ...................... 239/707

(Continued)

*Primary Examiner* — Len Tran
*Assistant Examiner* — Justin Jonaitis
(74) *Attorney, Agent, or Firm* — Muirhead and Saturnelli, LLC

(57) ABSTRACT

An explosive and narcotics detection system detects the presence of trace particles of those materials that are adhering to surfaces. In order to detect such particles, it is necessary to first dislodge or release them from the surface, next to transport them to the detection instrument, and last to accumulate them on or in a particle collection device associated with the instrument. Narcotics and explosive particles are often bound tenaciously to the surface, and simple techniques, such as blowing air, will either remove only the largest particles or none at all. A nozzle to release particles of narcotics and explosives employs a coaxial configuration that permits particle release at an increased distance from the nozzle compared to existing devices.

13 Claims, 7 Drawing Sheets

U.S. PATENT DOCUMENTS 5,152,462 A * 10/1992 Evans .......................... 239/304
5,390,854 A * 2/1995 Hench .......................... 239/337
5,934,566 A * 8/1999 Kanno et al. .................. 239/398
5,942,699 A * 8/1999 Ornath et al. ............... 73/863.21
6,610,977 B2 * 8/2003 Megerle ........................ 250/287
6,883,721 B2 * 4/2005 Marin et al. ...................... 239/8

* cited by examiner

TRACE CHEMICAL PARTICLE RELEASE NOZZLE

CROSS-REFERENCE TO RELATED APPLICATIONS

This application is a Continuation-in-part of U.S. application Ser. No. 11/492,672, filed. Jul. 25, 2006 now abandoned, which is a Continuation-in-part of U.S. Ser. No. 11/258,477, filed Oct. 25, 2005 now U.S. Pat. No. 8,122,756, and which claims priority to Provisional Application 60/708,017, filed Aug. 12, 2005, and which is a Continuation-in-part of U.S. Ser. No. 10/890,820, filed Jul. 14, 2004 (now U.S. Pat. No. 7,098,672), which is a Continuation-in-part of U.S. Ser. No. 10/818,434, filed Apr. 5, 2004 (now U.S. Pat. No. 6,870,155), which is a Continuation-in-part of U.S. Ser. No. 10/349,491, filed Jan. 22, 2003 (now U.S. Pat. No. 6,828,795), which is a Continuation-in-part of U.S. Ser. No. 10/295,039, filed Nov. 14, 2002 (abandoned), and which is a Continuation-in-part of U.S. Ser. No. 10/295,010, filed Nov. 14, 2002 (now U.S. Pat. No. 6,861,646), which claims priority from Provisional Application 60/363,485, filed Mar. 12, 2002, and Provisional Application 60/357,618, filed Feb. 15, 2002, and Provisional Application 60/357,394, filed Feb. 15, 2002, all of which are incorporated herein by reference.

This application is also a Continuation-in-part of U.S. application Ser. No. 11/248,603, filed Oct. 12, 2005 now U.S. Pat. No. 7,576,320, which is a Continuation-in-part of U.S. Ser. No. 10/890,820, filed Jul. 14, 2002 (now U.S. Pat. No. 7,098,672), and which is a Continuation-in-part of U.S. Ser. No. 10/853,563, filed May 25, 2004 now U.S. Pat. No. 7,244,288, which is a Continuation-in-part of U.S. Ser. No. 10/818,434, filed Apr. 5, 2004 (now U.S. Pat. No. 6,870,155), which is a Continuation-in-part of U.S. Ser. No. 10/754,088, filed Jan. 7, 2004 (now U.S. Pat. No. 6,888,128), which claims priority from Provisional Application 60/473,649, filed May 28, 2003, and Provisional Application 60/363,485, filed Mar. 12, 2002, and Provisional Application 60/363,485, filed Mar. 12, 2002, and Provisional Application 60/363,485, filed Mar. 12, 2002, and Provisional Application 60/363,485, filed Mar. 12, 2002, and Provisional Application 60/357,394, filed Feb. 15, 2002, and Provisional Application 60/357,618, filed Feb. 15, 2002, and Provisional Application 60/357,394, filed Feb. 15, 2002, and Provisional Application 60/357,618, filed Feb. 15, 2002, and Provisional Application 60/357,394, filed Feb. 15, 2002, and Provisional Application 60/357,618, filed Feb. 15, 2002, and Provisional Application 60/357,394, filed Feb. 15, 2002, and Provisional Application 60/357,618, filed Feb. 15, 2002, all of which are incorporated herein by reference.

BACKGROUND OF THE INVENTION

1. Field of the Invention

This application relates to detection of chemical traces of substances such as explosives or narcotics and, more particularly, to the dislodging and release of particles of substances from a surface in order to facilitate the transport, capture, detection, and identification of the particles.

2. Description of Related Art

There exist a wide variety of instruments that are capable of detecting and identifying particles of narcotics and explosives once the sample of particles is transported to the instrument and subsequently vaporized. Examples include, but are not limited to, ion mobility spectrometers, mass spectrometers, gas chromatographs, surface acoustic wave sensors, cantilever beam sensors, and electron capture detectors. Similarly, there are several ways commonly employed to transport said particles to the instrument, some of which are incorporated within the instrument and some requiring an operator to perform the transfer. Examples include, but are not limited to, mechanically transporting a collected sample to the instrument, vacuum collection of vapor or particles, and vortex vacuum sampling.

In the above examples, the particles begin by being attached to a surface by weak chemical bonds, van der Waals forces, mechanical attachment in a fibrous structure or porosity, electrostatic attraction, or entrainment in a sticky material, such as grease. For narcotics and explosives particles, the surface adhesion forces can be relatively strong, making the particles difficult to remove by simple, low momentum transfer methods, such as blowing a puff of air. Removal of such strongly adhered particles by blowing air is usually successful only for the largest, heaviest particles that present the greatest surface area to the blowing air. In general, blowing air does not readily remove particles of explosives or narcotics from rigid surfaces, only from flexible surfaces such as cloth, where the fluttering motion of the material provides the momentum to mechanically dislodge the particles, or from unstable surfaces, such as cardboard, where the substrate material can flake off together with the target particle. Even with cloth, the blowing air stream usually requires a very high velocity flow to have any effect and then only for the largest particles, so the process is very inefficient. Surfaces subject to blowing air during normal usage, such as the sides of a vehicle, are particularly difficult for obtaining a trace chemical sample simply by employing an air jet.

The distance between the target surface and the blowing air jet is also relevant. Air jets from nozzles are known to diverge and slow in velocity with distance traversed due to interaction with the surrounding atmosphere, making them lose efficiency for particle removal with increasing standoff distance. A nozzle that employs an aerosol including pressurized gas and solid particles in order to enhance target particle release is similarly affected, and the aerosol particles slow rapidly with standoff distance.

In some cases, the process of taking a sample begins with an operator or a machine physically wiping an absorbent, often textured substance, such as chemical filter paper, onto the surface to be tested. Particles of the chemical of interest may then be transferred and concentrated on or in the surface texture of the absorber by the mechanical action of the wiping. This intermediate absorber is then brought to the vicinity of the detection instrument to make a measurement. The wiping method generally works reliably and efficiently but can be costly, because the media usually has to be replaced often.

There are many applications in which it is desirable to avoid having to manually wipe a surface. These include sampling without an operator, large area sampling, remote sampling, robotic sampling, and situations in which the frequent replacement of wiping materials is not acceptable. In these cases the use of a jet or a jet containing an aerosol to dislodge and release target particles from the surface can be employed, but the decreasing velocity of the delivered gas or aerosol particles limits the useful standoff distance. In particular, even a simple nozzle can be very efficient for particle release if it is located a short distance from the target surface or operates with a dangerously high delivery pressure.

Accordingly, it would be desirable to provide a high efficiency particle release nozzle that operates at long distance using appropriate gas delivery pressures, for example of about 100 pounds per square inch.

SUMMARY OF THE INVENTION

According to the system described herein, a device for dislodging and releasing trace particles of explosives or narcotics from a target surface includes at least one nozzle and at least one controller. The at least one nozzle may include a first orifice for the emission of a first jet of pressurized gas towards the target surface and at least one second orifice for the emission of a second jet of pressurized gas directed towards the target surface, wherein a velocity of gas emitted by the second jet is equal to or greater than a velocity of gas emitted in the first jet. The at least one controller may control at least one of the first jet and the second jet, wherein the pulse of the second jet is emitted less than one second prior to the emission of the pulse from the first jet, and the pulse of the second jet is on during the pulse of the first jet. A pulse may be less than one second. The at least one second orifice may be coaxial to the first orifice, and the at least one second orifice may include a single orifice or a plurality of orifices arrayed concentric to the first nozzle. The system may further include a source of pulsed pressurized gas for the first jet and a source of pulsed pressurized gas for the second jet. At least one electrically controlled valve may control at least one of the pulse of the first jet and the pulse of the second jet. The at least one second orifice may emit a pulse substantially parallel to the pulse emitted from the first jet. The controller may include a computer-controlled timer, time delay relays and/or timed electrical circuits and may turn on the first jet and the at least one second jet simultaneously.

According further to the system described herein, a device for dislodging and releasing trace particles of explosives or narcotics from a target surface includes at least one nozzle and at least one controller. The at least one nozzle may include a first orifice for the emission of a first jet of an aerosol directed towards the target surface, wherein the aerosol includes a mixture of pressurized gas and solid particles, and at least one second orifice for the emission of a second jet of pressurized gas directed towards the target surface, wherein a velocity of gas emitted by the second jet is equal to or greater than a velocity of gas and solid particles emitted in the first jet. The at least one controller may control at least one of the first jet and the second jet, wherein the pulse of the second jet is emitted less than one second prior to the emission of the pulse from the first jet, and the pulse of the second jet is on during the pulse of the first jet. A pulse may be less than one second. The at least one second orifice may be coaxial to the first orifice, and the at least one second orifice may include a plurality of orifices arrayed concentric to the first nozzle. The system may further include a source of pulsed pressurized gas for the first jet and a source of pulsed pressurized gas for the second jet. At least one electrically controlled valve may control at least one of the pulse of the first jet and the pulse of the second jet. The at least one second orifice may emit a pulse substantially parallel to the pulse emitted from said first jet. The controller may include a computer-controlled timer, time delay relays and/or timed electrical circuits and may turn on the first jet and the at least one second jet simultaneously.

According further to the system described herein, a chemical detection system for detecting trace quantities of narcotics or explosives includes a particle release component that releases particles from a target surface, a particle collection component that collects the particles, and a particle transport component that transports the particles from the target surface to the particle collection component. The particle collection component may include at least one nozzle and at least one controller. The at least one nozzle may include a first orifice for the emission of a first jet of pressurized gas towards the target surface and at least one second orifice for the emission of a second jet of pressurized gas directed towards the target surface, wherein a velocity of gas emitted by the second jet is equal to or greater than a velocity of gas emitted in the first jet.

The at least one controller may control at least one of the first jet and the second jet, wherein the pulse of the second jet is emitted less than one second prior to the emission of the pulse from the first jet, and the pulse of the second jet is on during the pulse of the first jet. A pulse is preferably less than one second. The at least one second orifice may be coaxial to the first orifice and be at least one of: a single orifice coaxial to the first orifice and a plurality of orifices arrayed concentric to the first orifice According further to the system described herein, the particle release component may include a nozzle for a coaxial gas jet or a coaxial aerosol jet, either of which may be provided with a source of pressurized gas and directed towards a target surface that may be contaminated with traces of narcotics or explosives related chemicals. The source of pressurized gas may be operated continuously or preferably be pulsed. A pulse may be preferably less than one second. The pressure of the pressurized gas may be about one hundred pounds per square inch, a value easily obtained with small compressors, but significantly higher pressures may also be employed, limited only by the availability, cost, and safety restrictions for the pressurized gas. For example, a high pressure tank of gas may not be acceptable in a public area due to the risk of explosion caused by mishandling.

According further to the system described herein, a nozzle is provided for guiding the jets of gas or the mixture of aerosol particles and blowing gas towards a point on the target surface such that this point is the object of the particle transport component of the said particle collection system.

According further to the system described herein, the coaxial nozzle provides two sources of blowing air, a central orifice for a first jet and at least one second orifice for a second jet. If a single orifice is employed for the second jet, the second orifice may be disposed concentric to and surrounding the central orifice for the first jet. If a plurality of orifices is employed for the second jet, the plurality of orifices may be disposed in a ring surrounding and coaxial with the central orifice for the first jet. The plurality of orifices may be aimed parallel with and blowing in the direction of the first jet or they may be aimed to focus their collective jets towards the axis defined by the first jet with the focal point located beyond the orifice of the first jet in the direction of the target surface.

According further to the system described herein, the coaxial nozzle is operated such that the velocity of the gas in the plurality of second jets may be equal to or greater than the velocity of the gas in the first jet. This arrangement of velocities holds the gas or aerosol of the first jet in a tighter bundle, thus avoiding the tendency of the gas to spread as the gas in the jet interacts with the surrounding atmosphere. The effect of holding the gas in a tighter bundle is enhanced by increasing the velocity of the gas in the plurality of second jets relative to the first jet. In addition, faster relative velocity of the gas in the plurality of second jets transfers energy to the gas or aerosol particles in the first jet, further increasing the velocity of the gas or aerosol particles at long distance from the coaxial nozzle.

According further to the system described herein, the aerosol particles may be solid. Solid particles may have a minimal vapor pressure at ambient temperature, that is, they do not significantly evaporate, they may sublime at ambient temperature, or they may melt at ambient temperature. An example of the first would be particles of silica, an example of the second would be particles of dry ice, frozen carbon dioxide, and an example of the third would be particles of frozen water ice. Further, an aerosol generator may be provided with a reservoir of particles such that a measured quantity is provided with each puff of said pressurized gas.

According further to the system described herein, the aerosol particle material is selected to provide no significant damage to the target surface. Aerosol particles with a high hardness, such as silica or alumina, are abrasive and may damage the target surface. A soft particle with a Mohs scale hardness less than or about equal to 4, such as the mineral talc (magnesium silicate), is preferred. Other candidate materials include, but are not limited to, plastic microspheres, diatomaceous earth, Mohs=1-1.5, Fuller's earth (magnesium aluminum silicate), Mohs=1½-2, blackboard chalk (gypsum, calcium sulfate), Mohs=2, kaolin (alumina silicate), Mohs=2, sodium bicarbonate, Mohs=3, and natural chalk ($CaCO_3$), Mohs=3. Except for the plastic microspheres, these materials are oxides and have no flashpoint, an important characteristic when working with finely divided materials. The particle sizes are less than 250 micrometers and preferably between 1 and 50 micrometers.

According further to the system described herein, the aerosol particle material is selected to be non-toxic and harmless to humans and animals, as long as the aerosol is not directed into the eyes. Talc, for example, may be used as a skin treatment for babies, because of its softness, inertness, and affinity for adsorbing organic compounds. Talc is also commonly available in a variety of particle sizes and is inexpensive. Sodium bicarbonate is an ingredient in bread and other food products and is commonly available in a variety of particle sizes and is inexpensive.

According further to the system described herein, the aerosol particles may impact the target particles on the target surface and provide sufficient momentum transfer to dislodge said target particles from said target surface and become entrained in the puff of air transporting the aerosol particles. The dislodged target particles and aerosol particles may then be collected by the particle transport component.

According further to the system described herein, the particle transport component may be a simple vacuum suction flow into a nozzle or a vacuum suction flow into a nozzle that is bounded circumferentially by a spinning vortex. In either case, the aerosol particles and dislodged target particles are swept into the vacuum suction flow and transported to a particle collecting medium associated with the said particle collection system.

According further to the system described herein, the particle collection component may be any of a variety of particle collecting techniques. Examples include, but are not limited to, a mesh filter, a woven three dimensional mesh, a filter made of commonly employed filter materials, an absorbent surface that may be chemically coated to enhance adhesion, a vortex particle separator, an electrostatic particle collector, a particle impactor, and an engineered material with finely etched openings to pass air but retain particles.

BRIEF DESCRIPTION OF THE DRAWINGS

Embodiments of the system are described with reference to the several figures of the drawing, in which.

DETAILED DESCRIPTION OF VARIOUS EMBODIMENTS

Figures 1A, 1B:
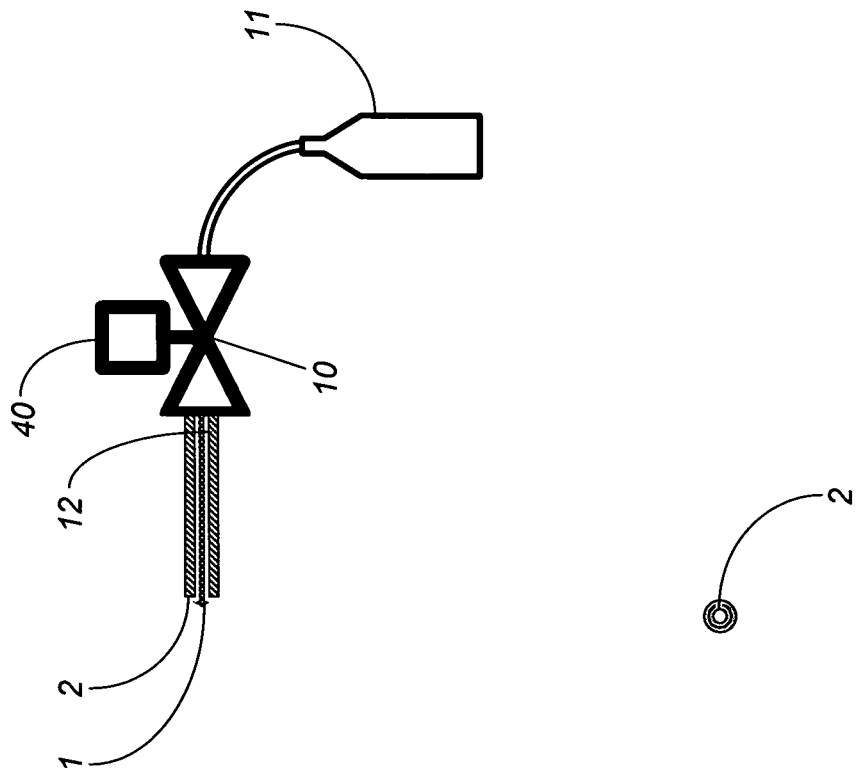
FIG. 1A is a schematic diagram of a conventional tubular nozzle used in existing systems.
FIG. 1B is a cross-section of the nozzle shown in FIG. 1A.

FIG. 1A shows a conventional tubular nozzle having basic features for releasing target particles based on the existing state-of-the-art. FIG. 1B is a cross-section of the nozzle shown in FIG. 1A. The nozzle includes a central tubular jet with an orifice 2 with gas pressure supplied through a valve 10 from pressure source 11. A controller 40 that may be operated by a remote control system is used to open valve 10 for a brief interval, for example fifty milliseconds, to send a burst of high velocity gas at a target surface. The gas flow 12 is indicated by an arrow 1 showing the direction of flow.

Figures 2A, 2B:
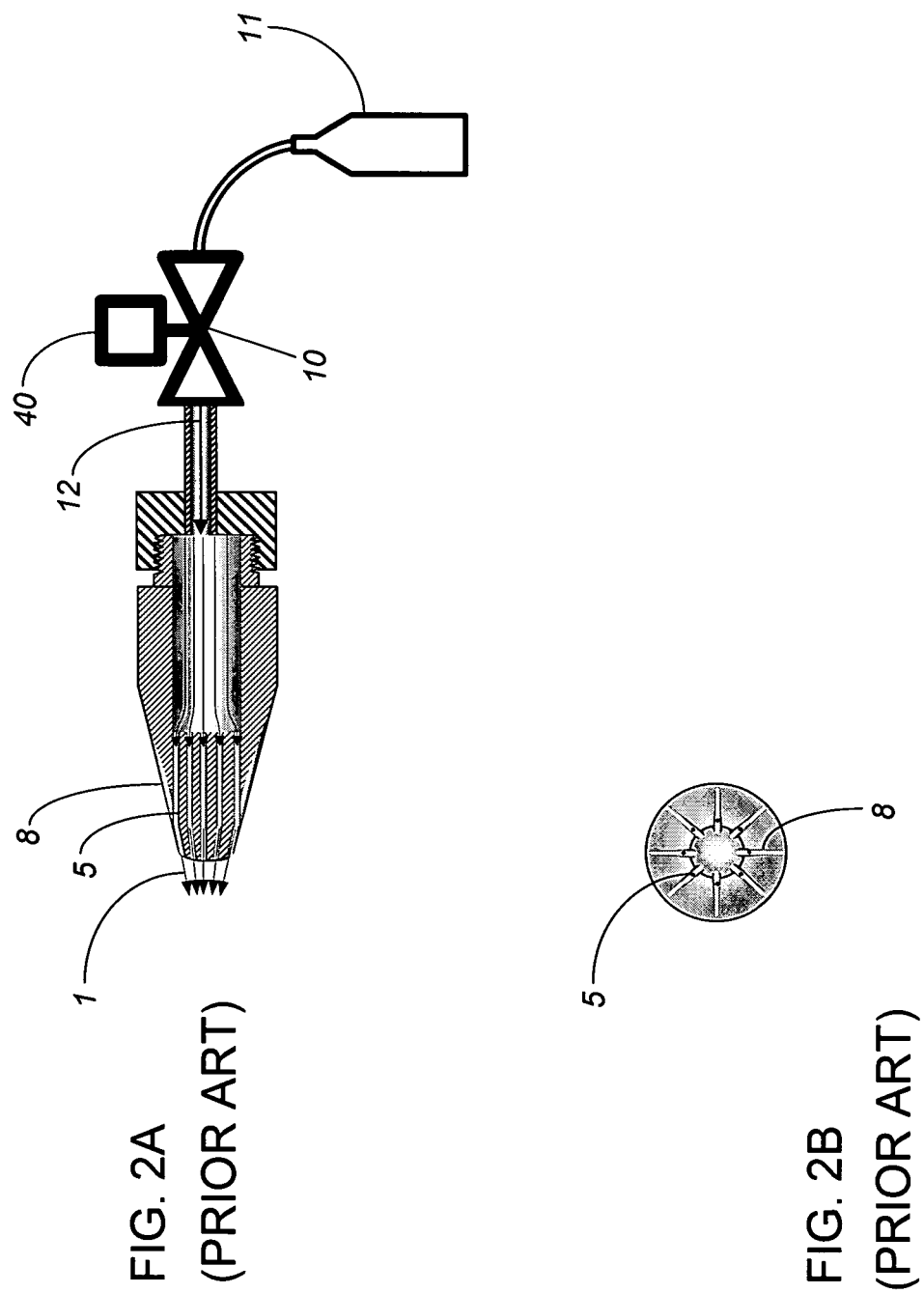
FIG. 2A is a schematic diagram showing a conventional nozzle used in existing systems including an array of nozzles that are all focused on the axis of the array.
FIG. 2B is a cross-section of the nozzle shown in FIG. 2A.

FIG. 2A shows another conventional tubular nozzle having basic features for releasing target particles based on the existing state-of-the-art. FIG. 2B is a cross-section of the nozzle shown in FIG. 2A. The nozzle includes a plurality of first orifices 5 for multiple jets that are focused to converge beyond the nozzle on its central axis and thus merge into a single jet at a distance from the nozzle. Slots 8 are employed to entrain surrounding air and enhance the quantity of gas that may be directed away from the nozzle. Gas pressure is supplied through a valve 10 from pressure source 11. A controller 40 that may be operated by a remote control system is used to open valve 10 for a brief interval, for example fifty milliseconds, to send a burst of high velocity gas at a target surface. The gas flow 12 is indicated by arrows 1 showing the direction of flow.

Figure 3A:
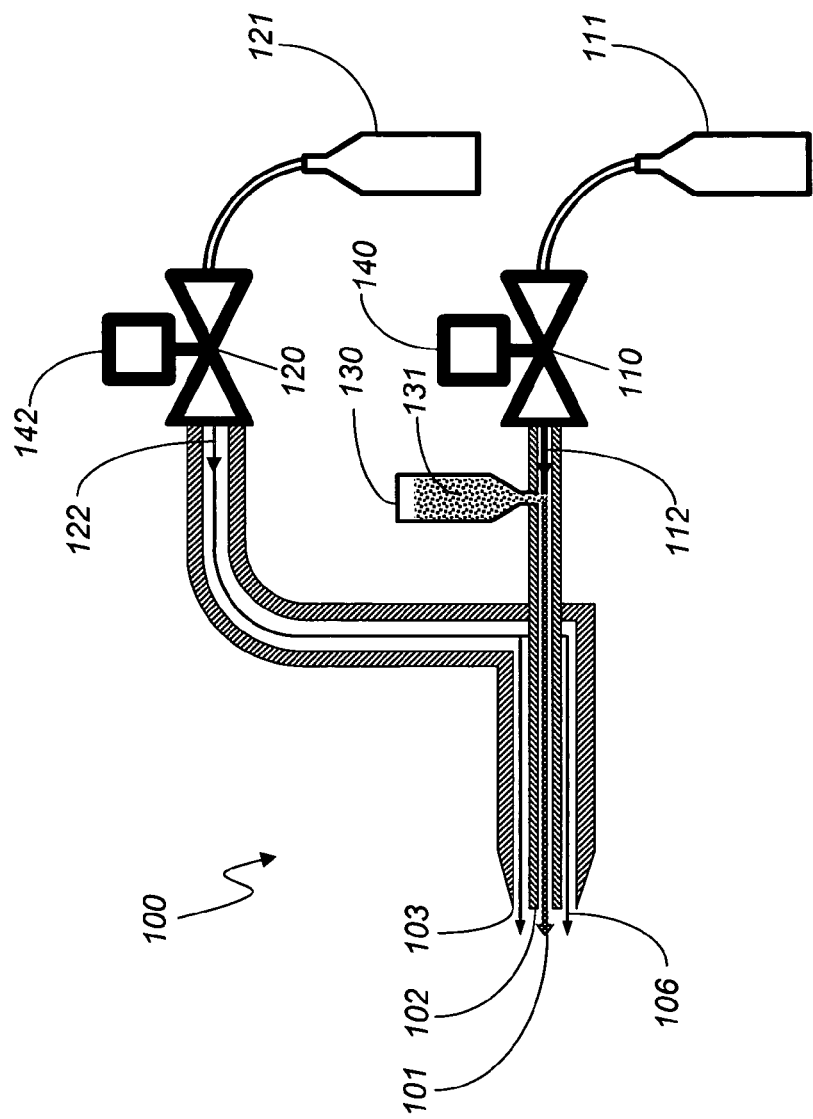
FIG. 3A is a schematic diagram showing an embodiment for a coaxial nozzle, according to the system described herein, in which a single second jet has an orifice that is concentric to and surrounding the central orifice of the first jet.
Figure 3B:
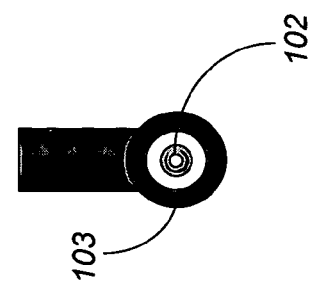
FIG. 3B is a cross-section of the nozzle shown in FIG. 3A.

FIG. 3A shows a coaxial nozzle 100 according to an embodiment of the system described herein for blowing at target surfaces to release target particles of explosives or narcotics. FIG. 3B is a cross-section of the nozzle shown in FIG. 3A. While various embodiments may differ in details, FIG. 3A shows basic features of the coaxial gas jet nozzle 100 for releasing target particles as described herein. The nozzle 100 may include a central tubular jet with a first orifice 102 with gas pressure supplied through a valve 110 from pressure source 111. The pressure of the pressurized gas may be about 100 pounds per square inch, a value easily obtained with small compressors, but significantly higher pressures may also be employed, limited only by the availability, cost, and safety restrictions for the pressurized gas. For example, a high pressure tank of gas may not be acceptable in a public area due to the risk of explosion caused by mishandling. The source of pressurized gas may be operated continuously or be pulsed. In an embodiment, a pulse is preferably less than one second.

A controller 140 that may be operated by a remote control system may be used to open valve 110 for a brief interval, for example fifty milliseconds, to send a burst of high velocity gas at a target surface. The gas flow 112 is indicated by an arrow 101 showing the direction of flow. A second orifice 103 may be disposed concentric to and surrounding the first orifice 102 and arranged so that the second jet is aimed parallel to and in the same direction as the jet from the first orifice 102. Optionally, the second jet may be aimed to focus or defocus its gas flow in order to modify the resultant spot size on the target surface. Gas pressure for second orifice 103 is supplied through a valve 120 from pressure source 121. It may be convenient to operate the nozzle with a single pressure source 111 and adjust the relative gas velocities from the first jet and second jet using the relative cross sectional areas of the two orifices. However, a second gas pressure source may be optionally employed as shown in FIG. 3A. A second controller 142 that may be operated by a remote control system may control valve 120. Alternatively, the controller 142 and the controller 140 may be a single controller. The gas flow 122 is indicated by an arrow 106 showing the direction of flow.

The nozzle 100 may be operated such that the velocity of the gas in the second jet is equal to or greater than the velocity of the gas in the first jet. This arrangement of velocities may hold the gas or aerosol of the first jet in a tighter bundle, thus avoiding the tendency of the gas to spread as the gas in the jet interacts with the surrounding atmosphere. The effect of holding the gas in a tighter bundle may be enhanced by increasing the velocity of the gas in the second jet relative to the first jet. In addition, faster relative velocity of the gas in the second jet transfers energy to the gas or aerosol particles in the first jet, further increasing the velocity of the gas or aerosol particles at long distance from the coaxial nozzle.

The gas in the first jet may also contain solid particles 131 of an aerosol supplied from reservoir 130 in order to further enhance the efficiency of target particle release. An aerosol may be defined as particles of a solid intermixed with a carrier gas. The solid particles may have a minimal vapor pressure at ambient temperature, that is, solid particles that do not significantly evaporate, the solid particles may sublime at ambient temperature, and/or the solid particles may melt at ambient temperature. An example of minimal vapor pressure particles would be particles of silica, an example of the particles that sublime at room temperature would be particles of dry ice, frozen carbon dioxide, and an example of the particles that melt at ambient temperature would be particles of frozen water ice. Further, the aerosol particle material may be selected to be non-toxic and harmless to humans and animals. For example, talc may be used, which is non-toxic to humans due to its softness, inertness, and affinity for adsorbing organic compounds, and is available in a variety of particle sizes and is inexpensive. A second example is particles of sodium bicarbonate, which is an ingredient in bread and other food products. It is available in a variety of particle sizes and is inexpensive.

The aerosol particle material may be selected to provide no significant damage to the target surface. Aerosol particles with a high hardness, such as silica or alumina, are abrasive and may damage the target surface. A soft particle with a Mohs scale hardness less than or about equal to 4, such as the mineral talc (magnesium silicate), may be preferred. Other candidate materials include, but are not limited to, plastic microspheres, diatomaceous earth, Mohs=1-1.5, Fuller's earth (magnesium aluminum silicate), Mohs=1½-2, blackboard chalk (gypsum, calcium sulfate), Mohs=2, kaolin (alumina silicate), Mohs=2, sodium bicarbonate, Mohs=3, and natural chalk ($CaCO_3$), Mohs=3. Except for the plastic microspheres, these materials are oxides and have no flashpoint, an important characteristic when working with finely divided materials. The particle sizes are less than two hundred fifty micrometers and preferably between one and fifty micrometers. An aerosol generator may be provided with a reservoir of particles such that a measured quantity is provided with each puff of the pressurized gas.

Figure 4A:
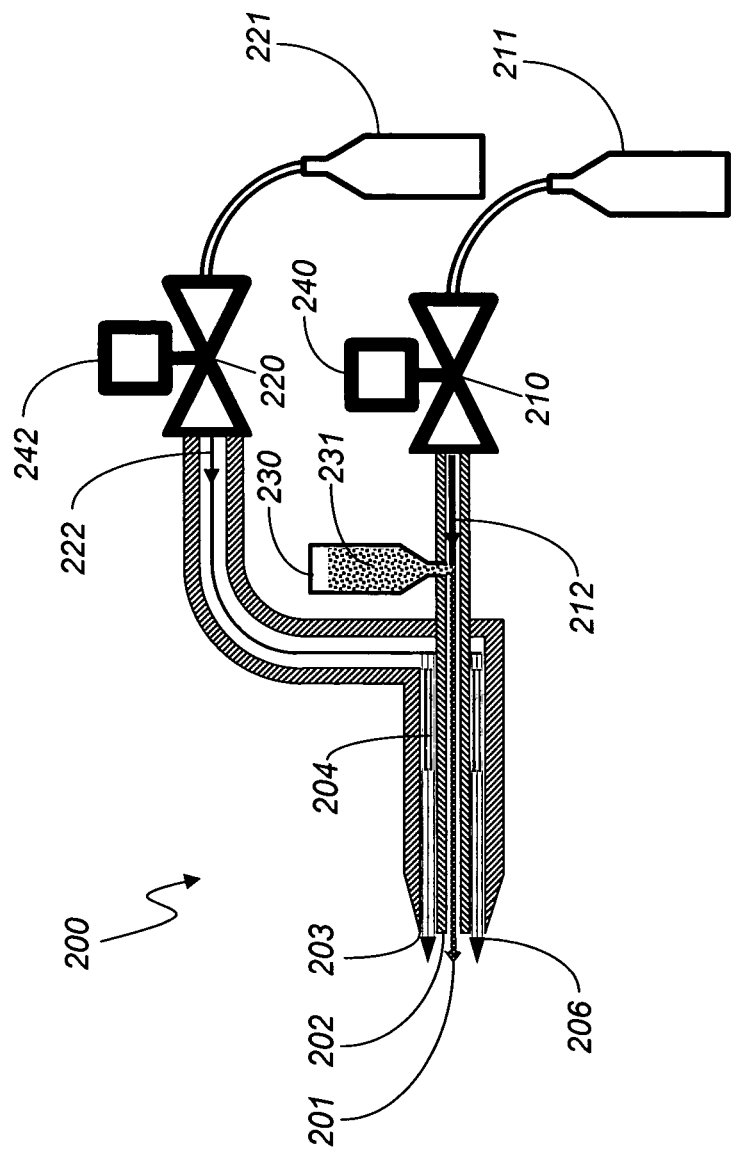
FIG. 4A is a schematic diagram showing an embodiment for a coaxial nozzle, according to the system described herein, in which a single second jet has an orifice that is concentric to and surrounding the central orifice of the first jet and includes internal guide orifices that direct the transmitted air parallel to the axis of the first jet.
Figure 4B:
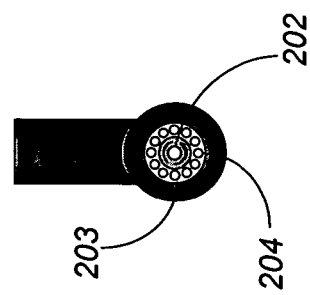
FIG. 4B is a cross-section of the nozzle shown in FIG. 4A.

FIG. 4A shows a coaxial nozzle 200 according to another embodiment of the system described herein for blowing at target surfaces to release target particles of explosives or narcotics. FIG. 4B is a cross-section of the nozzle shown in FIG. 4A. While various embodiments may differ in details, FIG. 4A shows basic features of the coaxial gas jet nozzle 200 for releasing target particles as described herein. The nozzle 200 may include a central tubular jet with a first orifice 202 with gas pressure supplied through a valve 210 from pressure source 211. A controller 240 that may be operated by a remote control system may be used to open valve 210 for a brief interval, for example fifty milliseconds, to send a burst of high velocity gas at a target surface. The gas flow 212 is indicated by an arrow 201 showing the direction of flow. In this embodiment a second orifice 203 is disposed concentric to and surrounding the first orifice 202 and arranged so that the second jet is aimed parallel to and in the same direction as the jet from the first orifice 202. Optionally, the second jet may be aimed to focus or defocus its gas flow in order to modify the resultant spot size on the target surface. It is recognized that said aiming may in part occur in a mixing region within the nozzle. Gas pressure for second orifice 203 may be supplied through a valve 220 from pressure source 221. It may be convenient to operate the nozzle with a single pressure source 211 and adjust the relative gas velocities from the first jet and second jet using the relative cross sectional areas of the two orifices. However, a second gas pressure source 221 may optionally be employed as shown in FIG. 4A. The gas entering the path for the second jet may not be moving parallel to the axis of the first jet, because the gas enters at right angles to the axis of the first jet. Guide tubes 204 may be included within the nozzle structure to straighten the flow of the gas from the second jet. A second controller 242 that may be operated by a remote control system may control valve 220. Alternatively, the controller 242 and the controller 240 may be a single controller. The gas flow 222 is indicated by an arrow 206 showing the direction of flow. The gas in the first jet may also contain solid particles 231 of an aerosol supplied from reservoir 230 in order to further enhance the efficiency of target particle release.

Figure 5A:
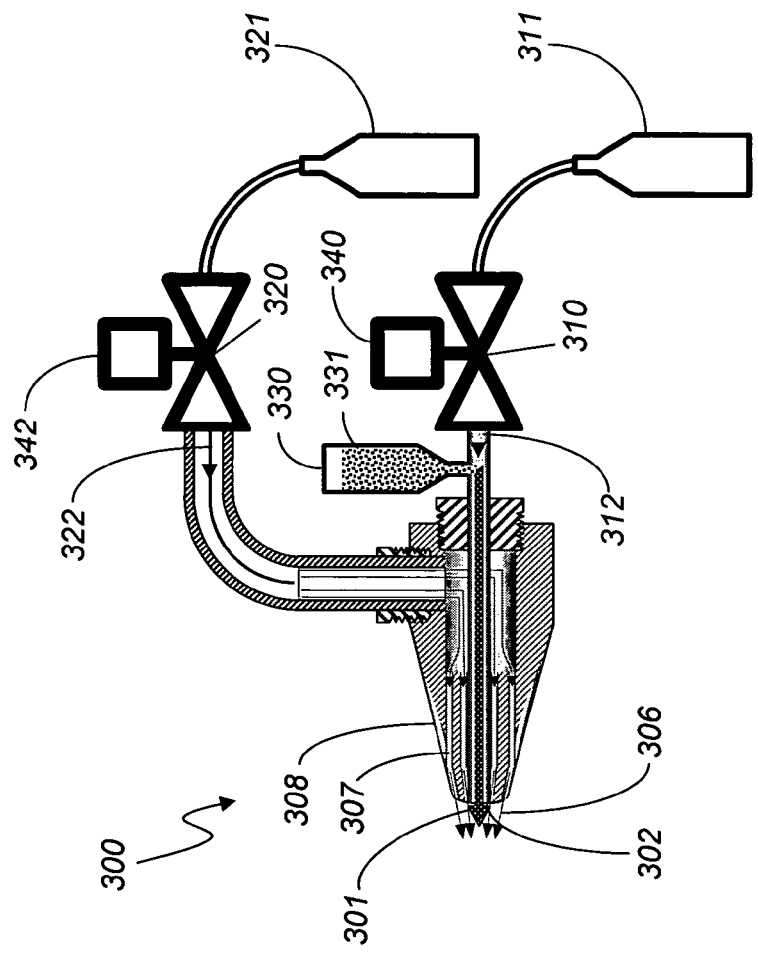
FIG. 5A is a schematic diagram showing an embodiment for a coaxial nozzle, according to the system described herein, in which a plurality of second jets has orifices that surround the central orifice of the first jet and focus the jets towards the axis of the first jet in the direction of the target surface.
Figure 5B:
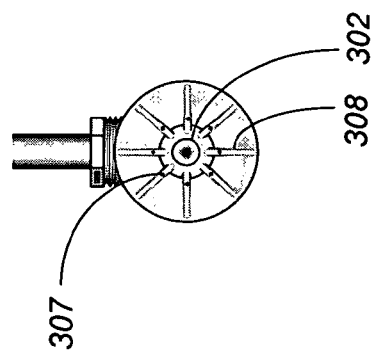
FIG. 5B is a cross-section of the nozzle shown in FIG. 5A.

FIG. 5A shows a coaxial nozzle 300 according to another embodiment of the system described herein for blowing at target surfaces to release target particles of explosives or narcotics. FIG. 5B is a cross-section of the nozzle shown in FIG. 5A. While various embodiments may differ in details, FIG. 5A shows basic features of the coaxial gas jet nozzle 300 for releasing target particles as described herein. The nozzle 300 may include a central tubular jet with a first orifice 302 with gas pressure supplied through a valve 310 from pressure source 311. A controller 340 that may be operated by a remote control system may be used to open valve 310 for a brief interval, for example fifty milliseconds, to send a burst of high velocity gas at a target surface. The gas flow 312 is indicated by an arrow 301 showing the direction of flow. The nozzle 300 may further include a plurality of orifices 307 for multiple jets that are focused to converge beyond the nozzle on its central axis. Optionally, the plurality of second jets may be aimed parallel or defocused in order to modify the resultant spot size on the target surface. It is recognized that said aiming may in part occur in a mixing region within the nozzle. Slots 308 may be employed to entrain surrounding air and enhance the quantity of gas that may be directed away from the nozzle. Gas pressure may be supplied through a valve 320 from a pressure source 321. A controller may be used to open valve 320 for a brief interval, for example fifty milliseconds, to send a burst of high velocity gas at a target surface. The gas flow 322 is indicated by an arrow 306 showing the direction of flow. It may be convenient to operate the nozzle with a single pressure source 311 and adjust the relative gas velocities from the first jet and second jet using the relative cross sectional areas of the orifices. However, the second gas pressure source 321 may be optionally employed as shown in FIG. 5. A second controller 342 that may be operated by a remote control system may control valve 320. Alternatively, the controller 342 and the controller 340 may be a single controller. The gas flow 322 is indicated by an arrow showing the direction of flow. The gas in the first jet may also contain solid particles 331 of an aerosol supplied from reservoir 330 in order to further enhance the efficiency of target particle release.

The controller 140, 240, 340 for opening and closing valves 110, 210, 310 and the controller 142, 242, 342 for opening and closing valves 120, 220, 320 in FIGS. 3-5 may be arranged to open both valves at the same time or to open valve 120, 220, 320 earlier than valve 110, 210, 310. Opening valve 120, 220, 320 earlier may help to open a path through the stagnant atmosphere and further enhance the tightness of the bundle of gas from the first jet. The controller 140, 240, 340 may include a computer-controlled timer, time delay relays, and/or timed electrical circuits.

Figure 6:
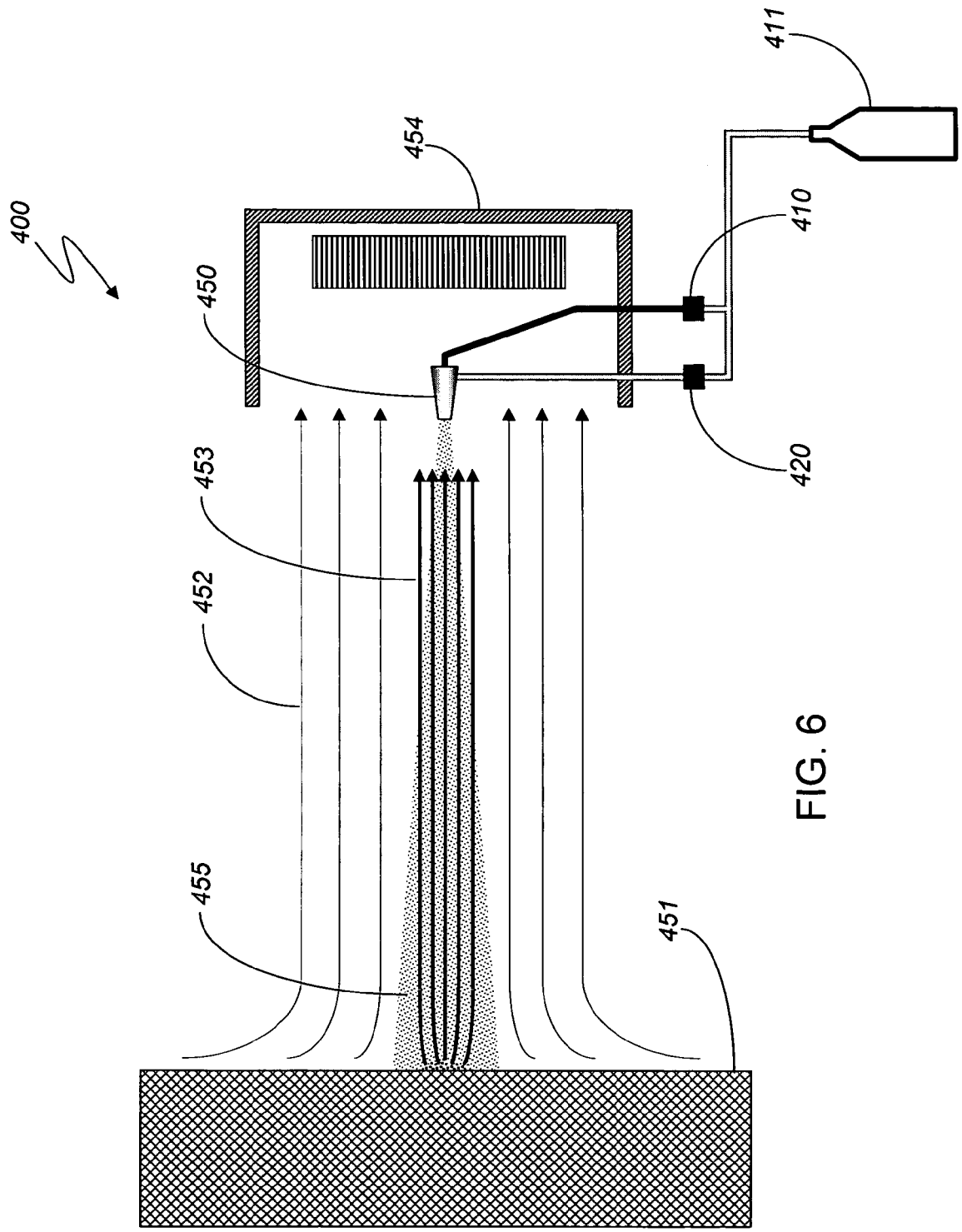
FIG. 6 is a schematic diagram showing a possible configuration for the use of the high standoff distance coaxial nozzle for releasing target particles of explosives and narcotics from a vertical surface, according to an embodiment of the system described herein.

FIG. 6 shows a system 400 having a configuration for employing a high standoff distance coaxial nozzle 450 according to an embodiment of the system described herein. The target surface 451 may be disposed with its normal direction substantially parallel with the axis of the nozzle 450. The combined jet flow of both the first and second orifices 455 from nozzle 450 may be dispersed in a narrow cone that maintains the gas or optional aerosol particles at a high or even increasing velocity for a long distance from the nozzle 450. Tests have shown good particle release as far as sixty centimeters from nozzle 450. Nozzle 450 may be disposed within the suction zone of the particle collection system 454 in order to efficiently collect the released particles 453 within a particle transport system 452, such as a sample suction flow. Pressurized gas may be provided from source 411 and controlled with valves 410, 420 as further described elsewhere herein The particle collection system 454 may include any of a variety of particle collecting mechanisms. Examples include, but are not limited to, a mesh filter, a woven three dimensional mesh, a filter made of commonly employed filter materials, an absorbent surface that may be chemically coated to enhance adhesion, a vortex particle separator, an electrostatic particle collector, a particle impactor, and an engineered material with finely etched openings to pass air but retain particles.

The particle transport system 454 may include, for example, a simple vacuum suction flow into a nozzle and/or a vacuum suction flow 452 into a nozzle that is bounded circumferentially by a spinning vortex. The aerosol particles may impact the target particles on the target surface and provide sufficient momentum transfer to dislodge said target particles from said target surface 451 and become entrained in the puff of gas transporting the aerosol particles. The dislodged target particles and aerosol particles 453 may then be collected by the particle transport system 454. The aerosol particles and dislodged target particles may be swept into the vacuum suction flow and transported to a particle collecting medium associated with the particle collection system.

Figure 7:
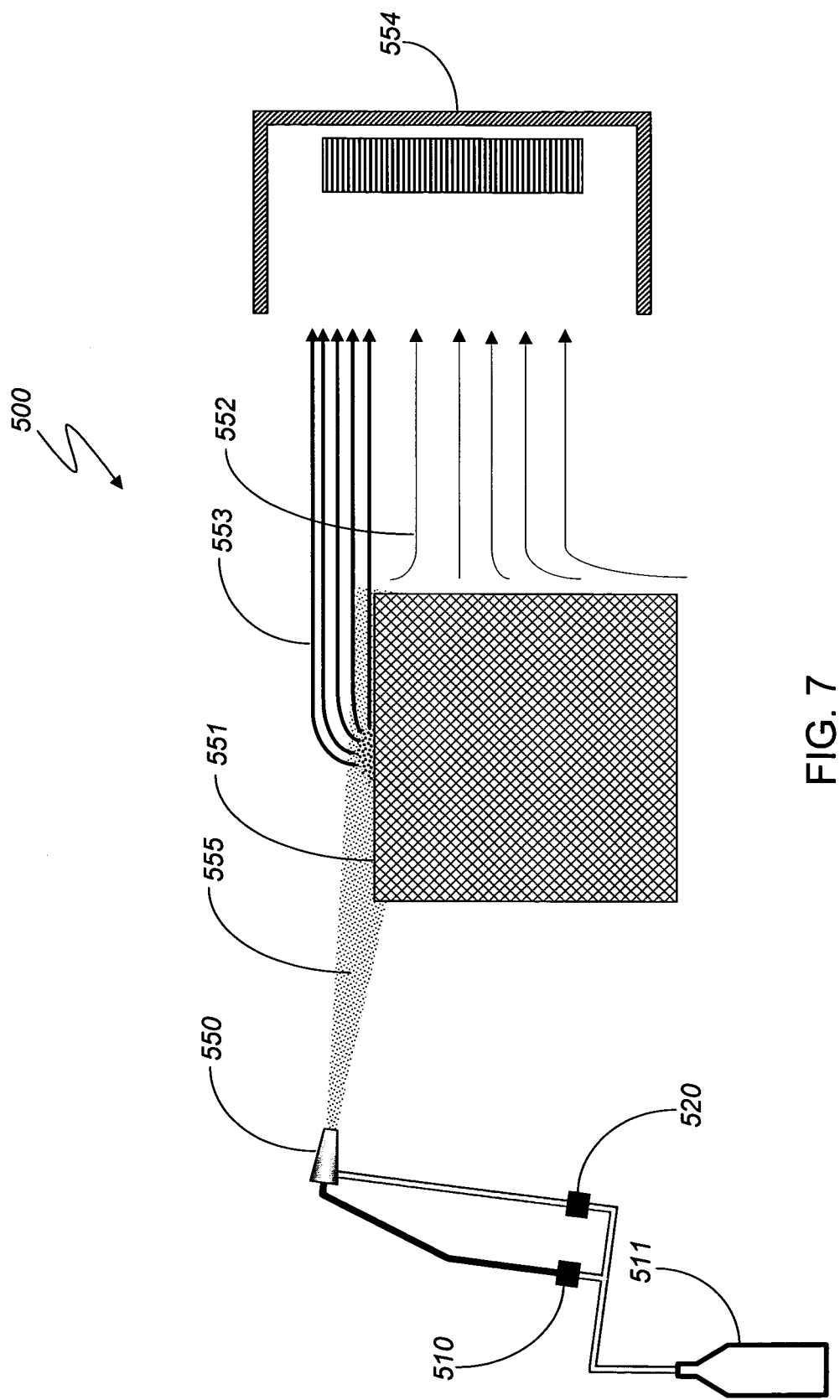
FIG. 7 is a diagram showing a second possible configuration for the use of the high standoff distance coaxial nozzle for releasing target particles of explosives and narcotics from a horizontal surface, according to an embodiment of the system described herein.

FIG. 7 shows a system 500 having another configuration for employing a high standoff distance coaxial nozzle 550 according to an embodiment of the system described herein. The target surface 551 may be disposed with its normal direction substantially but not exactly perpendicular to the axis of the nozzle 550. The combined jet flow of both the first and second orifices 555 from nozzle 550 may be dispersed in a narrow cone that maintains the gas or optional aerosol particles at a high or even increasing velocity for a long distance from nozzle 550. The nozzle 550 may be aimed close to tangential to the target surface 551 with the nozzle 550 disposed opposite to the location of the particle collection system 554 in order to use the flow from the nozzle to direct the target particles 553 by blowing them towards the particle collection system 554 as well as employing entrainment within the sample collection suction flow of the particle transport system 552. Pressurized gas may be provided from source 511 and controlled with valves 510, 520 as further described elsewhere herein The system described herein may incorporate any combination of the embodiments discussed herein as well as other features, such as features described in commonly assigned copending applications and/or issued U.S. patents, such as U.S. Application No. 60/708,017, filed Oct. 25, 2005, U.S. Pat. No. 6,861,646, U.S. Pat. No. 6,870,155, and U.S. Pat. No. 6,888,128, which are all incorporated herein by reference, and/or other patents or patent applications incorporated herein by reference.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method for dislodging and releasing particles of explosives or narcotics from a target surface, comprising:
providing at least one nozzle, the nozzle including a first orifice for the emission of a first jet of pressurized gas directed towards said target surface and at least one second orifice for the emission of a second jet of pressurized gas directed towards said target surface, wherein a velocity of gas emitted by said second jet is equal to or greater than a velocity of gas emitted in said first jet;
controlling at least one of: the first jet and the second jet using at least one controller, wherein controlling the at least one of: the first jet and the second jet includes emitting the pulse of said second jet at less than one second prior to the emission of the pulse from said first jet, and maintaining the pulse of said second jet during the pulse of said first jet, and wherein said velocity of said at least one second jet is controlled by the ratio of the cross section of the orifice of said at least one second jet compared to the cross section of the orifice of said first jet.

2. The method for dislodging and releasing particles according to claim 1, further comprising:
   providing a source of pulsed pressurized gas for the first jet; and
   providing a source of pulsed pressurized gas for the second jet.

3. The method for dislodging and releasing trace particles according to claim 1, further comprising:
   controlling at least one of: the pulse of the first jet and the pulse of the second jet using at least one electrically controlled valve.

4. The method for dislodging and releasing particles according to claim 1, wherein said pressurized gas is at least one of air, nitrogen, carbon dioxide, and argon.

5. The method for dislodging and releasing particles, according to claim 1, wherein said at least one second orifice emits at least one pulse substantially parallel to the axis of the pulse emitted from said first jet.

6. The method for dislodging and releasing particles according to claim 1, wherein said at least one second orifice emits at least one pulse that is focused towards the pulse emitted from said first jet or defocused from the pulse emitted from said first jet.

7. The method for dislodging and releasing particles according to claim 2, wherein said velocity of said at least one second jet is controlled by the pressure of said source of pulsed pressurized gas for said second jet.

8. The method for dislodging and releasing particles according to claim 1, wherein said controller includes at least one of: a computer-controlled timer, time delay relay, and timed electrical circuit.

9. The method for dislodging and releasing particles according to claim 1, wherein the said controller turns on said first jet and said at least one second jet simultaneously.

10. The method for dislodging and releasing particles according to claim 1,
    wherein the first jet of pressurized gas further includes an aerosol wherein the aerosol includes a mixture of pressurized gas and solid particles.

11. A chemical detection system, comprising:
    a particle release component that releases particles from a target surface;
    a particle collection component that collects the particles; and
    a particle transport component that transports the particles from the target surface to the particle collection component,
    wherein the particle release component includes:
    at least one nozzle, the at least one nozzle including:
       a first orifice for the emission of a first jet of pressurized gas directed towards said target surface; and
       at least one second orifice for the emission of a second jet of pressurized gas directed towards said target surface, wherein a velocity of gas emitted by said second jet is equal to or greater than a velocity of gas emitted in said first jet;
    at least one controller that controls at least one of: the first jet and the second jet, wherein the pulse of said second jet is emitted less than one second prior to the emission of the pulse from said first jet, and the pulse of said second jet is on during the pulse of said first jet, and wherein said velocity of said at least one second jet is controlled by the ratio of the cross section of the orifice of said at least one second jet compared to the cross section of the orifice of said first jet.

12. The chemical detection system according to claim 11, wherein the first jet is an aerosol jet, the aerosol jet including the pressurized gas and solid particles.

13. The method for dislodging and releasing particles according to claim 1, wherein said at least one second orifice is at least one of: a single orifice coaxial to said first orifice and a plurality of orifices arrayed concentric to said first orifice.

* * * * *